United States Patent
Irish et al.

(10) Patent No.: US 10,120,214 B2
(45) Date of Patent: Nov. 6, 2018

(54) SYSTEMS AND METHODS FOR LIGHT BEAM POSITION DETECTION

(71) Applicant: QUALCOMM Incorporated, San Diego, CA (US)

(72) Inventors: Linda Irish, San Diego, CA (US); Russell Gruhlke, San Jose, CA (US); Manav Raina, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 235 days.

(21) Appl. No.: 15/192,811

(22) Filed: Jun. 24, 2016

(65) Prior Publication Data

US 2018/0095304 A1    Apr. 5, 2018

(51) Int. Cl.
| | |
|---|---|
| G01B 11/14 | (2006.01) |
| G02F 1/11 | (2006.01) |
| G01J 3/02 | (2006.01) |
| G01J 3/44 | (2006.01) |
| G06F 3/042 | (2006.01) |
| G01S 7/481 | (2006.01) |
| G02B 26/10 | (2006.01) |
| G01N 21/359 | (2014.01) |
| G01N 21/17 | (2006.01) |

(52) U.S. Cl.
CPC ............ *G02F 1/113* (2013.01); *G01J 3/0289* (2013.01); *G01J 3/44* (2013.01); *G01S 7/4814* (2013.01); *G01S 7/4817* (2013.01); *G01S 7/4818* (2013.01); *G02B 26/103* (2013.01); *G06F 3/0423* (2013.01); *G01N 21/359* (2013.01); *G01N 2021/1738* (2013.01); *G06T 2207/10052* (2013.01)

(58) Field of Classification Search
CPC .... G01S 7/4812; G01S 7/4817; G01S 7/4818; A61B 1/00165; A61B 1/00172; A61B 5/0062; G02B 2006/0098; G02B 26/10; G02B 26/103; G02F 1/113; G01J 3/44; G01J 3/0289; G01N 21/359; G06F 3/0423
USPC ............. 356/614–623, 121–124; 250/227.26
See application file for complete search history.

(56) References Cited

U.S. PATENT DOCUMENTS

| | | | |
|---|---|---|---|
| 5,317,148 A | 5/1994 | Gray et al. | |
| 6,845,190 B1 * | 1/2005 | Smithwick | ........... A61B 1/0008 385/1 |

(Continued)

OTHER PUBLICATIONS

International Search Report and Written Opinion—PCT/US2017/034004—ISA/EPO—dated Aug. 31, 2017.

*Primary Examiner* — Hoa Pham
(74) *Attorney, Agent, or Firm* — Kilpatrick Townsend & Stockton

(57) ABSTRACT

Disclosed herein are techniques for determining the position of a light beam on a beam shaping device. A feature can be formed on the beam shaping device to affect at least a portion of a light beam when the feature is illuminated by the light beam. When the light beam is directed onto the feature on the beam shaping device, a feature detection signal may be generated by a detector in response to detecting at least the portion of the light beam affected by the feature that has been illuminated by the light beam. The position of the light beam on the beam shaping device at a time instant can then be determined based, at least in part, on the feature detection signal.

30 Claims, 9 Drawing Sheets

(56) References Cited

U.S. PATENT DOCUMENTS

| | | | |
|---|---|---|---|
| 6,856,712 B2* | 2/2005 | Fauver | G02B 6/241 |
| | | | 385/12 |
| 8,988,317 B1 | 3/2015 | Liang et al. | |
| 2005/0052644 A1 | 3/2005 | Lewis et al. | |
| 2006/0195014 A1* | 8/2006 | Seibel | A61B 1/0008 |
| | | | 600/102 |
| 2008/0198365 A1 | 8/2008 | Treado et al. | |
| 2009/0244260 A1* | 10/2009 | Takahashi | A61B 1/00172 |
| | | | 348/45 |
| 2010/0295825 A1 | 11/2010 | Ting | |
| 2013/0293882 A1 | 11/2013 | Dottery et al. | |
| 2014/0231647 A1 | 8/2014 | Chinn et al. | |
| 2016/0154234 A1 | 6/2016 | McMorrow | |
| 2017/0248783 A1* | 8/2017 | Gruhlke | G01S 7/4817 |
| 2018/0045816 A1* | 2/2018 | Jarosinski | G01S 7/4814 |

* cited by examiner

SYSTEMS AND METHODS FOR LIGHT BEAM POSITION DETECTION

BACKGROUND

Light beams may be used to measure distances between objects. By way of example, a light detection and ranging (LIDAR) system is an active remote sensing system that can use light beams to obtain the range, i.e., distance, from a source to one or more points on a target. A LIDAR system uses a light beam (typically a laser beam) to illuminate at least a portion of the target and measures the time it takes for the emitted light beam from the source to arrive at the target and then return to a detector near the source or at a known location. In other words, the range from the source to the point on the target can be determined based on the time-of-flight (ToF) of the light beam from the source to the detector. To measure ranges to multiple points on a target or in a field-of-view of the LIDAR system, the laser beam is usually scanned in one or two dimensions. In various implementations of the LIDAR system, it is desirable to determine the position of a LIDAR beam at the transmitter of the LIDAR system in order to determine the position of the LIDAR beam at the target at a given time.

BRIEF SUMMARY

Techniques disclosed herein relate to determining the position of a light beam on a beam shaping device, such as a lens or a lens array, at or near a light source, for example, a transmitter of a LIDAR system or other like system. In various embodiments, artificial features can be made on the beam shaping device to create discontinuities or enhancements in the reflection, absorption, or transmission characteristics of the beam shaping device. The position of a light beam on the beam shaping device at a given time may be determined at least partially based on the detected discontinuities or enhancements in the reflected, adsorbed, or transmitted light from the beam shaping device caused by the artificial features of the bean shaping device.

In accordance with an example implementation, a system may include a beam shaping device including a feature configured to affect at least a portion of a light beam upon illumination by the light beam. The system may also include a beam directing device configured to direct the light beam onto the beam shaping device at different positions, the different positions including a location of the feature. The system may further include an optical detector configured to generate a feature detection signal in response to detecting at least the portion of the light beam affected by the feature that has been illuminated by the light beam; and a processor configured to determine a position of the light beam on the beam shaping device at a time based, at least in part, on the feature detection signal. In some embodiments, the feature is configured to affect at least the portion of the light beam upon illumination by the light beam by causing at least one of a detectable change in reflection of at least the portion of the light beam, a detectable change in transmission of at least the portion of the light beam, a detectable change in absorption of at least the portion of the light beam, or a detectable combination thereof.

In various embodiments of the system, the light beam may include a laser beam, and the beam shaping device may be configured to illuminate a point on a target with the laser beam. In some embodiments, the system may further include a pulsed fiber laser configured to generate the light beam. In some systems, the beam shaping device may include a lens, and the feature may include at least one of a line, a dent, or a particle formed on a surface of the lens or inside the lens. In some systems, the beam shaping device may include a plurality of lenses, and the feature may include a reflective coating in an area at a boundary of two lenses in the plurality of lenses. The plurality of lenses may be arranged in one of a one-dimensional array, a two-dimensional array, and a three-dimensional array.

In some systems, the beam directing device may include an optical fiber configured to guide the light beam and vibrate upon stimulation, such that the light beam is directed onto the beam shaping device at different positions when the optical fiber vibrates. In some systems, the optical fiber may include a cantilever portion having a floating end. In some systems, the beam directing device may include an actuator configured to stimulate the optical fiber such that the vibration of the optical fiber may result in a predetermined scan pattern of the light beam, such as a spiral pattern. The actuator may include one of a piezoelectric tube, a micro-electro-mechanical system (MEMS) actuator, an electromagnetic actuator, and an acoustic actuator.

In accordance with an example implementation, a method for use in detecting a position of a light beam is disclosed. The method may include controlling, by a controller, a beam directing device to direct the light beam onto a beam shaping device at different positions, where the beam shaping device may include a feature configured to affect at least a portion of the light beam upon illumination by the light beam, and the different positions may include a location of the feature. The method may further include generating, by a detector, a detection signal in response to detecting at least the portion of the light beam affected by the feature that has been illuminated by the light beam; and determining, by a processor, the position of the light beam on the beam shaping device at a time based, at least in part, on the detection signal. In some embodiments, the feature is configured to affect at least the portion of the light beam upon illumination by the light beam by causing at least one of a detectable change in reflection of at least the portion of the light beam, a detectable change in transmission of at least the portion of the light beam, a detectable change in absorption of at least the portion of the light beam, or a detectable combination thereof.

In some embodiments of the method for use in detecting the position of the light beam, the light beam may include a laser beam, and the beam shaping device may be configured to illuminate a point on a target with the laser beam. In some methods, the beam shaping device may include a lens, and the feature may include at least one of a line, a dent, or a particle formed on a surface of the lens or inside the lens. In some other methods, the beam shaping device may include a plurality of lenses, and the feature may include a reflective coating in an area at a boundary of two lenses in the plurality of lenses.

In some embodiments of the method for use in detecting the position of the light beam, the beam directing device may include an optical fiber configured to guide the light beam and vibrate upon stimulation, such that the light beam is directed onto the beam shaping device at different positions when the optical fiber vibrates. The optical fiber may include a cantilever portion having a floating end. The beam directing device may include an actuator configured to stimulate the optical fiber such that the vibration of the optical fiber may result in a predetermined scan pattern of the light beam, such as a spiral pattern. The actuator may include one of a piezoelectric tube, a micro-electro-mechanical system (MEMS) actuator, an electromagnetic actuator, and an acoustic actuator.

In accordance with another example implementation, an apparatus may be provided, which may include means for beam shaping that include a feature configured to affect at least a portion of a light beam upon illumination by the light beam. The apparatus may also include means for directing the light beam onto the means for beam shaping at different positions, where the different positions include a location of the feature. The apparatus may further include means for generating at least one detection signal in response to detecting at least the portion of the light beam affected by the feature that has been illuminated by the light beam; and means for determining a position of the light beam on the means for beam shaping at a time based, at least in part, on the detection signal. In some embodiments, the feature is configured to affect at least the portion of the light beam upon illumination by the light beam by causing at least one of a detectable change in reflection of at least the portion of the light beam, a detectable change in transmission of at least the portion of the light beam, a detectable change in absorption of at least the portion of the light beam, or a detectable combination thereof.

In various embodiments of the apparatus, the light beam may include a laser beam, and the beam shaping device may be configured to illuminate a point on a target with the laser beam. In some embodiments of the apparatus, the beam shaping device may include a lens, and the feature may include at least one of a line, a dent, or a particle formed on a surface of the lens or inside the lens. In some embodiments of the apparatus, the beam shaping device may include a plurality of lenses, and the feature may include a reflective coating in at area at a boundary of two lenses in the plurality of lenses.

In accordance with yet another example implementation, a non-transitory computer-readable storage medium including machine-readable instructions stored thereon is disclosed. The non-transitory computer-readable storage medium may include instructions that are executable by one or more processors for controlling, through a controller, a beam directing device to direct a light beam onto the beam shaping device at different positions, where the beam shaping device includes a feature configured to affect at least a portion of the light beam upon illumination by the light beam, and the different positions include a location of the feature. The non-transitory computer-readable storage medium may further include instructions for receiving a detection signal generated by a detector in response to detecting at least the portion of the light beam affected by the feature that has been illuminated by the light beam; and determining a position of the light beam on the beam shaping device at a time based, at least in part, on the detection signal. In some embodiments, the feature is configured to affect at least the portion of the light beam upon illumination by the light beam by causing at least one of a detectable change in reflection of at least the portion of the light beam, a detectable change in transmission of at least the portion of the light beam, a detectable change in absorption of at least the portion of the light beam, or a detectable combination thereof.

In various embodiments of the non-transitory computer-readable storage medium including machine-readable instructions, the light beam may include a laser beam, and the beam shaping device may be configured to illuminate a point on a target with the laser beam. In some embodiments, the beam shaping device may include a lens, and the feature may include at least one of a line, a dent, or a particle formed on a surface of the lens or inside the lens. In some embodiments, the beam shaping device may include a plurality of lenses, and the feature may include a reflective coating in an area at a boundary of two lenses in the plurality of lenses.

In some embodiments of the non-transitory computer-readable storage medium including machine-readable instructions, the beam directing device may include an optical fiber configured to guide the light beam and vibrate upon stimulation, such that the light beam is directed onto the beam shaping device at different positions when the optical fiber vibrates. The beam directing device may include an actuator configured to stimulate the optical fiber such that the vibration of the optical fiber may result in a predetermined scan pattern of the light beam.

BRIEF DESCRIPTION OF THE DRAWINGS

Aspects of the present disclosure are illustrated by way of example. Non-limiting and non-exhaustive aspects are described with reference to the following figures, wherein like reference numerals refer to like parts throughout the various figures unless otherwise specified.

DETAILED DESCRIPTION

Figure 1:
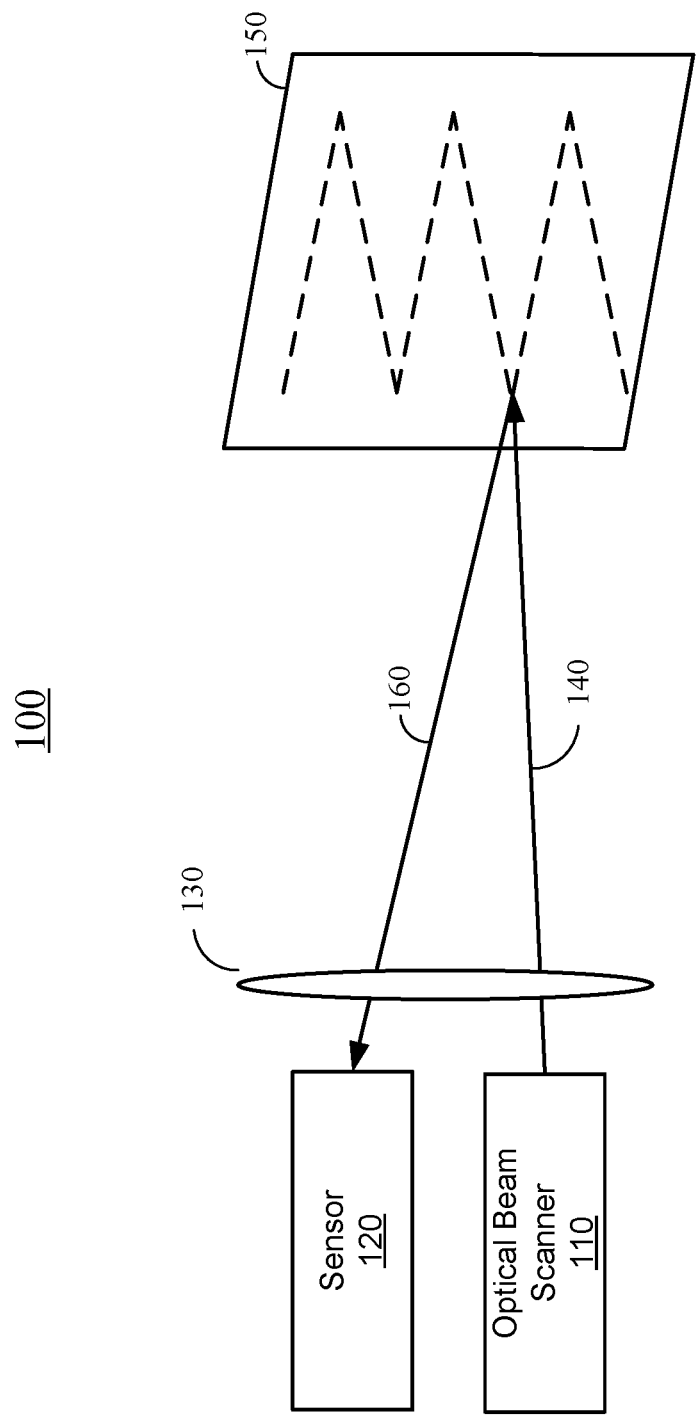
FIG. 1 is a simplified block diagram of an example light detection and ranging (LIDAR) system.

Several illustrative embodiments will now be described with respect to the accompanying drawings, which form a part hereof. The ensuing description provides embodiment (s) only, and is not intended to limit the scope, applicability or configuration of the disclosure. Rather, the ensuing description of the embodiment(s) will provide those skilled in the art with an enabling description for implementing an embodiment. It is understood that various changes may be made in the function and arrangement of elements without departing from the spirit and scope of this disclosure.

Techniques disclosed herein relate to determining the position of a light beam on a beam shaping (e.g., beam focusing, beam collimating, beam expanding, etc.) device, such as a lens or a lens array, at or near a light source, for example, a transmitter of a light detection and ranging (LIDAR) system or other like system. One or more (artificial) features can be made on the beam shaping device which may affect at least a portion of one or more light beams when illuminated by such. For example, certain one or more features may be configured/arranged to create discontinuities in the reflection, absorption or transmission characteristics of certain portions/points of the beam shaping device. When a light beam is scanned by a beam directing device according to a designed pattern, for example, the incident light beam on the beam shaping device may be affected (e.g., reflected, absorbed, transmitted, or the like or some combination thereof) by one or more such features in some manner different in comparison to other portions/points of the beam shaping device. The position of the light beam on the beam shaping device at a given time may then be determined based on the scanning properties of the beam directing device and the affects created by one or more illuminated features. In certain implementations, one or more features of a beam shaping device may affect at least a portion of a light beam (when illuminated at least in part thereby) in a manner that may be distinguishable from the affect(s) created by one or more other features of the beam shaping device. Hence, in certain implementations, it may be possible to determine that a particular feature(s) was/were illumined at a given time by the light beam.

A LIDAR system, also referred to as a laser detection and ranging (LADAR) system, is an active remote sensing system that can be used to obtain the range from a source to one or more points on a target. A LIDAR uses a light beam, typically a laser beam, to illuminate the one or more points on the target. Compared with other light sources, a laser beam may propagate over long distances without spreading significantly (highly collimated), and can be focused to small spots so as to deliver very high optical power densities and provide fine resolution. The laser beam may be modulated such that the transmitted laser beam includes a series of pulses. The transmitted laser beam may be directed to a point on the target, which may reflect the transmitted laser beam. The laser beam reflected from the point on the target can be measured, and the time-of-flight (ToF) from the time a pulse of the transmitted light beam is transmitted from the source to the time the pulse arrives at a detector near the source or at a known location may be measured. The range from the source to the point on the target may then be determined by, for example, r=c×t/2, where r is the range from the source to the point on the target, c is the speed of light in free space, and t is the ToF of the pulse of the light beam from the source to the detector.

FIG. 1 is a simplified block diagram of an example system 100, such as a LIDAR, LADAR, or other like system. System 100 may include an optical beam scanner 110, a sensor 120, and a lens 130. Optical beam scanner 110 may include an optical source, such as a laser, a laser diode, a vertical cavity surface-emitting laser (VCSEL), a light-emitting diode (LED), or other optical source. The laser may be, for example, an infrared pulsed fiber laser or other mode-locked laser with an output wavelength of, for example, 930-960 nm, 1030-1070 nm, around 1550 nm, or longer. Optical beam scanner 110 may also include a light directing device, such as a scanning stage, a piezoelectric actuator, or a MEMS device that can change the direction of the transmitted laser beam from the laser. Lens 130 may be used to collimate the transmitted laser beam from optical beam scanner 110 such that collimated laser beam 140 may propagate over a long distance to a target without spreading significantly. Lens 130 may also focus the transmitted laser beam from optical beam scanner 110 onto a small spot on the target. Lens 130 may also be used to expand the laser beam or divert the laser beam. As a result of the small beam spot, the resolution of system 100 may be improved.

Lens 130 may also be used to focus reflected laser beam 160 from a target 150 onto sensor 120 directly or into optical fibers connected to sensor 120. Sensor 120 may be a detector having a working (sensitive) wavelength comparable with the wavelength of the laser source. The detector may be a high speed photodetector, for example, a PIN photodiode with an intrinsic region between a p-type semiconductor region and a n-type semiconductor region, or an InGaAs avalanche photodetector (APD).

To measure ranges to multiple points on a target or in a field-of-view of a system, a laser beam is usually scanned in one or two dimensions as shown in FIG. 1. In order to achieve a 1-dimensional (1-D) or 2-dimensional (2-D) scan pattern, a system may use, for example, an array of lasers, multiple sets of lasers/sensors that are slightly tilted against each other, or a 2-D scanning mechanism, such that the laser beam may be scanned in, for example, a horizontal raster pattern and/or a vertical raster pattern as shown in FIG. 1.

There are many different types of laser beam scanning mechanisms, for example, a multi-dimensional mechanical stage, a Galvo-controlled mirror, a microelectromechanical (MEMS) mirror driven by micro-motors, a piezoelectric translator/transducer using piezoelectric material such as a quartz or lead zirconate titanate (PZT) ceramic, an electromagnetic actuator, or an acoustic actuator. Laser beam scanning may also be achieved without mechanical movement of any component, for example, using a phased array technique where phases of lasers in a 1-D or 2-D laser array may be changed to alter the wave front of the superimposed laser beam. In many of these scanning mechanisms, the position of the scanning beam may be determined based on the control signals that drive the scanning mechanisms, such that the system can determine the point on the target that reflects a particular transmitted light beam at a given time. For example, in FIG. 1, the position of the transmitted beam on lens 130 and thus the position of the transmitted beam on target 150 may be determined based on the signal that controls optical beam scanner 110 in system 100. As a more specific example, in a system with a MEMS mirror driven by micro-motors, the orientation of a MEMS micro-mirror may be determined based on the signal that controls the micro-motor that rotates the micro-mirror. The direction of the reflected beam by the micro-mirror and thus the position of the beam on the beam shaping device at a given time can then be determined based on the orientation of the micro-mirror at the given time.

Many of the above-described beam scanning mechanisms may be bulky and expensive. Alternatively or additionally, a resonant fiber scanning technique may be used to scan a laser beam. Due to the flexibility of the optical fiber, a wide field of view and a high resolution may be achieved. In addition, a resonant fiber beam scanner may be small and less expensive.

Figure 2:
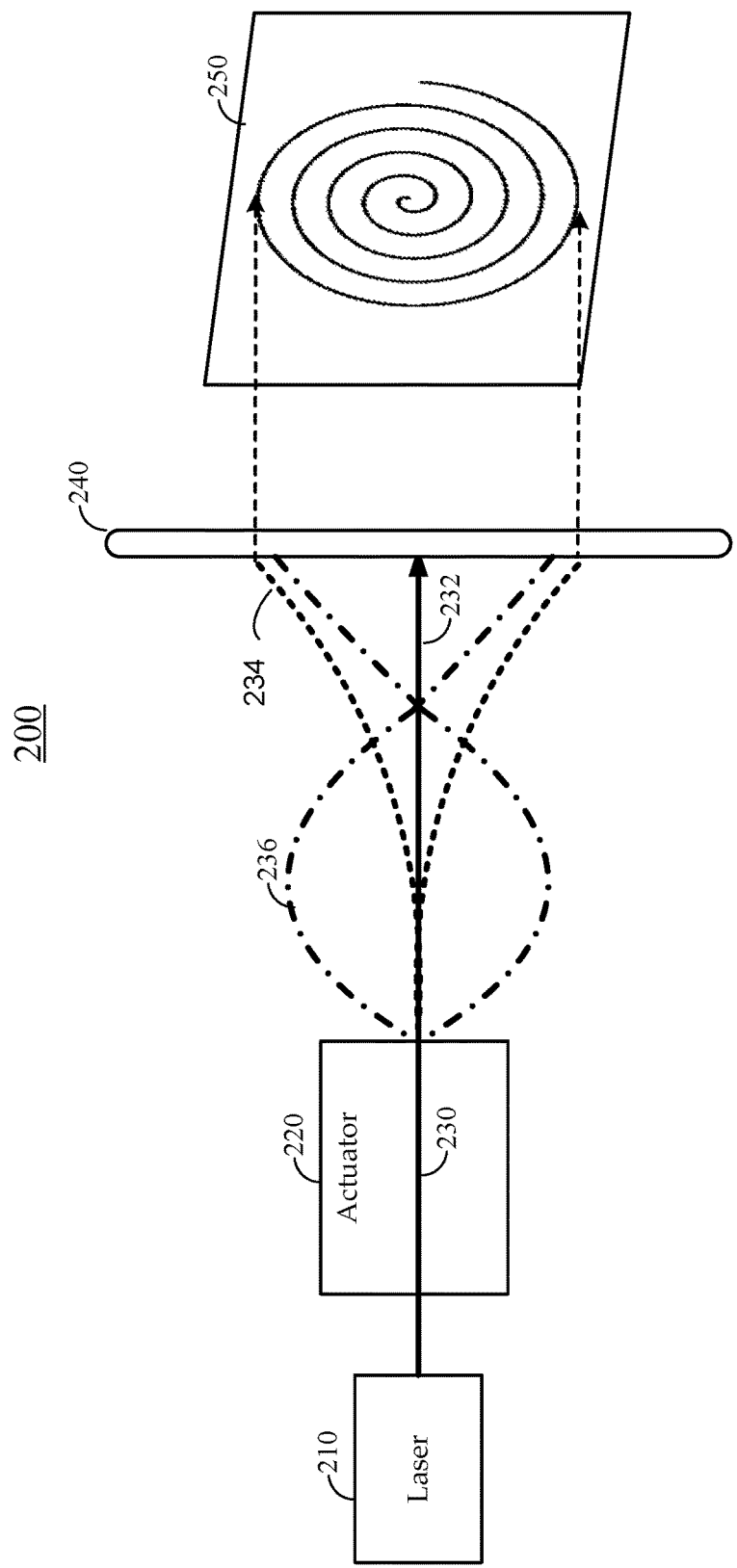
FIG. 2 illustrates an example system using a resonant optical fiber.

FIG. 2 illustrates an example system 200 using a resonant optical fiber. System 200 may be a LIDAR, LADAR, or other like system. System 200 may include a laser 210, an actuator 220, an optical fiber 230, and a beam shaping device 240, such as a lens or a lens array. Laser 210 may be a light source as described above with respect to optical beam scanner 110 of FIG. 1. Laser 210 may be a pulsed laser such as a mode-locked laser. Laser 210 may also include a modulator that can modulate the output beam of the laser.

The output beam of laser 210 is coupled to optical fiber 230, which carries the laser beam and guides it towards beam shaping device 240. Optical fiber 230 may be a single-mode fiber, a multi-mode fiber, or a bundle of fibers. Optical fiber 230 may pass through actuator 220, which may be, for example, a piezoelectric tube or other actuator as described above with respect to FIG. 1. A distal end 232 of optical fiber 230 may extend beyond actuator 220. Distal end 232 of optical fiber 230 extending beyond actuator 220 is flexible and can withstand a resonant motion caused by actuator 220 to act as a resonant cantilever. The low damping and resonant characteristics of the fiber enable the actuator to amplify a small actuator motion into a large fiber tip displacement. As a result, the laser beam emitted from the vibrating distal end 232 may produce laser beam scanning with a large field of view. The length of distal end 232 can be adjusted to achieve a desired resonant frequency and/or resonant mode. For example, as shown in FIG. 2, the length of distal end 232 of optical fiber 230 may be adjusted to achieve a resonant mode 234 with a single stationary node close to actuator 220 and a floating end (i.e., distal end 232), or a resonant mode 236 with two stationary nodes and a floating end (i.e., distal end 232).

A 2-D scan pattern can be produced with a single 2-axis actuator using a single fiber. For example, if the horizontal axis produces a constant amplitude sine wave, and the vertical axis produces a cosine wave with the same frequency and amplitude as the sine wave, a circle may result from a symmetric fiber. The scanning amplitudes on both x and y axes can be progressively decreased and/or increased to produce a spiral scan by progressively decreased and/or increased control signals. As a more specific example, if the horizontal vibration is a triangle amplitude modulated sinewave and the vertical vibration is a triangle amplitude modulated cosine wave, an evenly spaced spiral scan pattern may be generated. Beam shaping device 240 may then collimate the beam from distal end 232 of optical fiber 230 and project the collimated beam at a far field 250 to form an evenly spaced spiral scan pattern in far field 250 as shown in FIG. 2. In some embodiments, beam shaping device 240 may focus the beam from distal end 232 of optical fiber 230 to a small point in far field 250 in order to form a scan pattern in far field 250 with a higher scanning resolution.

In many systems, the actual scan pattern may not follow an ideal scan pattern as designed. For example, in system 200, due to the dynamics of the resonating fiber cantilever, the scan pattern may be distorted from the ideal pattern. Thus, in various systems, it is desirable to determine the position of the LIDAR beam at the transmitter of the systems and thus the position of the LIDAR beam on the target.

When a lens array is used in the optical system of a LIDAR, a greater angular amplification may be achieved. However, because of the optical refraction property of the lens, the direction of the light may be changed abruptly when the incident light crosses the boundary between two lenses.

Figure 3:
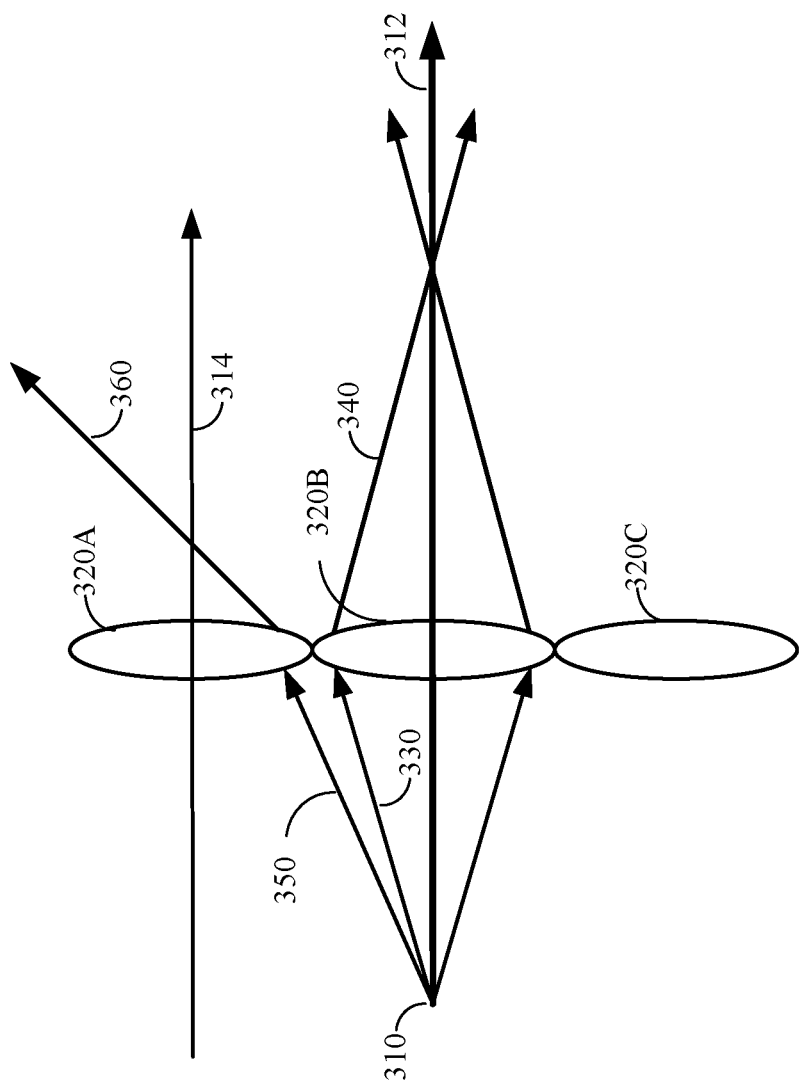
FIG. 3 illustrates the change of direction of the refracted light when the incident light crosses the boundary between two lenses.

FIG. 3 illustrates the change of direction of the refracted light when the incident light crosses the boundary between two lenses. As shown in FIG. 3, a light beam from a source 310 may be scanned and may irradiate a lens array including lenses 320A, 320B, and 320C. The light beam may irradiate lens 320B as shown by light beam 330 and be directed toward an optical axis 312 of lens 320B as shown by light beam 340. When the light beam is scanned vertically from bottom to top and crosses the boundary between lenses 320A and 320B, the light beam may irradiate lens 320A as shown by light beam 350 and be directed toward an optical axis 314 of lens 320A as shown by light beam 360. Light beam 360 and light beam 340 are propagating in very different directions. Thus, a discontinuity on the scan pattern at the target may result when the light beam crosses the boundary between two lenses. Therefore, it is also desirable to determine exactly when a LIDAR beam is crossing lens boundaries.

Figure 4:
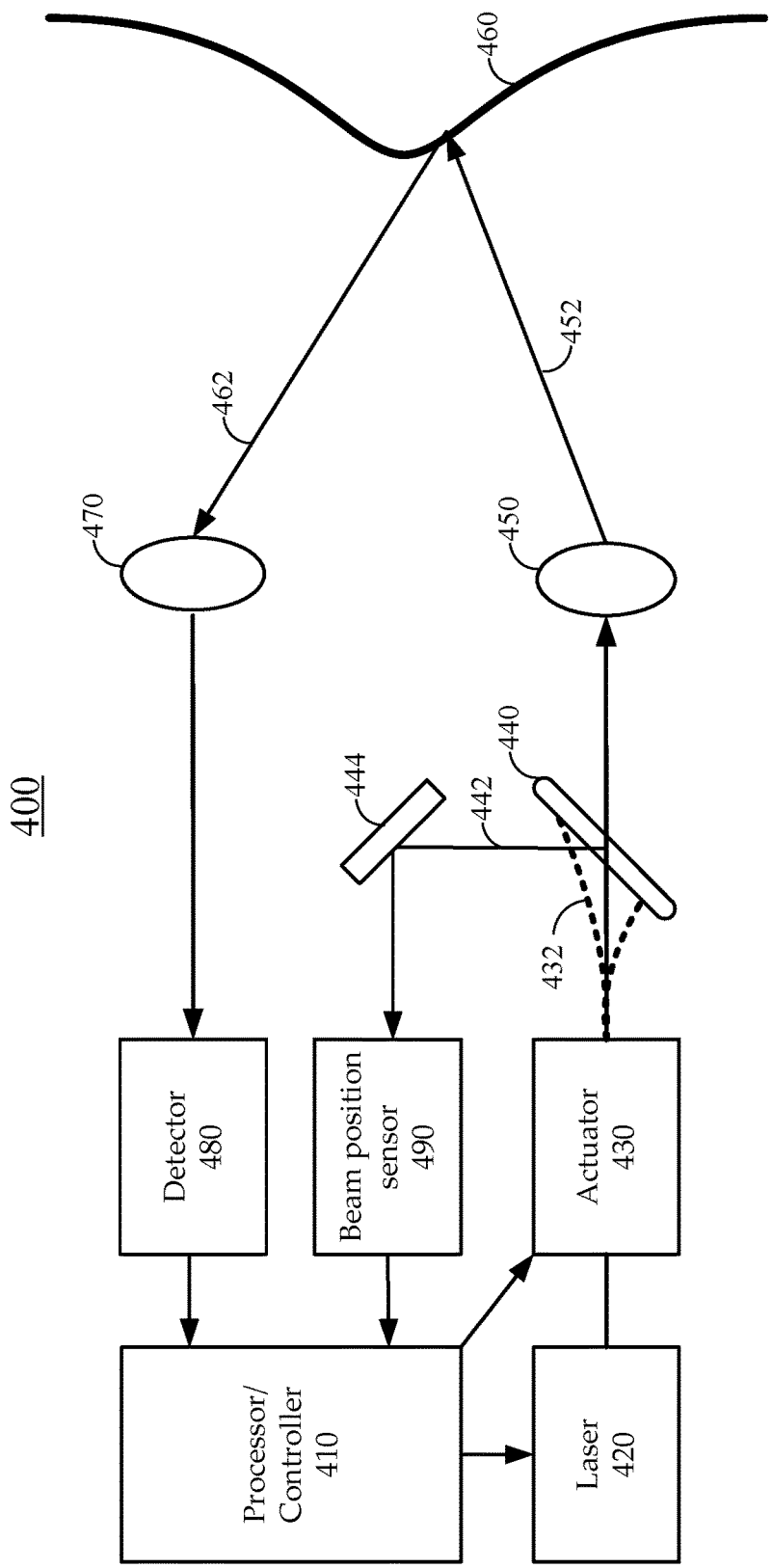
FIG. 4 illustrates an example system with a beam splitter for determining the position of the light beam at the transmitter.

FIG. 4 illustrates an example system 400 with a beam splitter for determining the position of a LIDAR beam at the LIDAR transmitter. System 400 may be a LIDAR, LADAR, or other like system. As in system 200 of FIG. 2, system 400 may include a laser 420, an optical fiber 432 coupled to laser 420 for guiding the output beam from laser 420, and an actuator 430 for stimulating optical fiber 432 to scan the output laser beam from laser 420. System 400 also includes a transmitter lens 450 for directing an incident laser beam towards a target 460 as shown by laser beam 452. Reflected laser beam 462 from target 460 may be collected by a receiver lens 470 and directed to a detector 480 as described above with respect to sensor 120 of FIG. 1. A processor/controller 410 may be used to synchronize and control the operations of laser 420, actuator 430, and detector 480, and analyze various points on target 460 based on the control signals for laser 420 and actuator 430, and the reflection signals detected by detector 480.

To detect the position of the laser beam on transmitter lens 450 and thus the position of the laser beam on target 460, a beam splitter 440 and a beam position sensor 490 may be added to system 400. Beam splitter 440 may split the output laser beam from optical fiber 432 and direct a portion of the output laser beam from optical fiber 432 towards beam position sensor 490 as shown by laser beam 442 in FIG. 4. Laser beam 442 may be directed to beam position sensor 490 by beam splitter 440 directly or indirectly through a mirror 444. Beam position sensor 490 may be a 2-D position sensing detector (PSD) that can detect laser beam 442. Processor/controller 410 or beam position sensor 450 may determine the position of the output laser beam from optical fiber 432 on beam splitter 440 or transmitter lens 450 based on the position (pixels) of the portion of beam position sensor 490 that detects laser beam 442.

As can be seen from FIG. 4, this method possibly suffers from loss of light, high complexity, and high cost. For example, with the addition of beam splitter 440, a portion of the incoming light beam is diverted to beam position sensor 490. In addition, in systems using a resonant fiber for beam scanning, the addition of the beam splitter for sampling the laser output can make it difficult to position the resonant fiber close enough to the beam shaping device (such as a lens or lens array), for example, transmitter lens 450, for best performance. Thus, accuracy achieved by this method may be insufficient for certain applications requiring high precision LIDAR beam position determination.

Figure 5A:
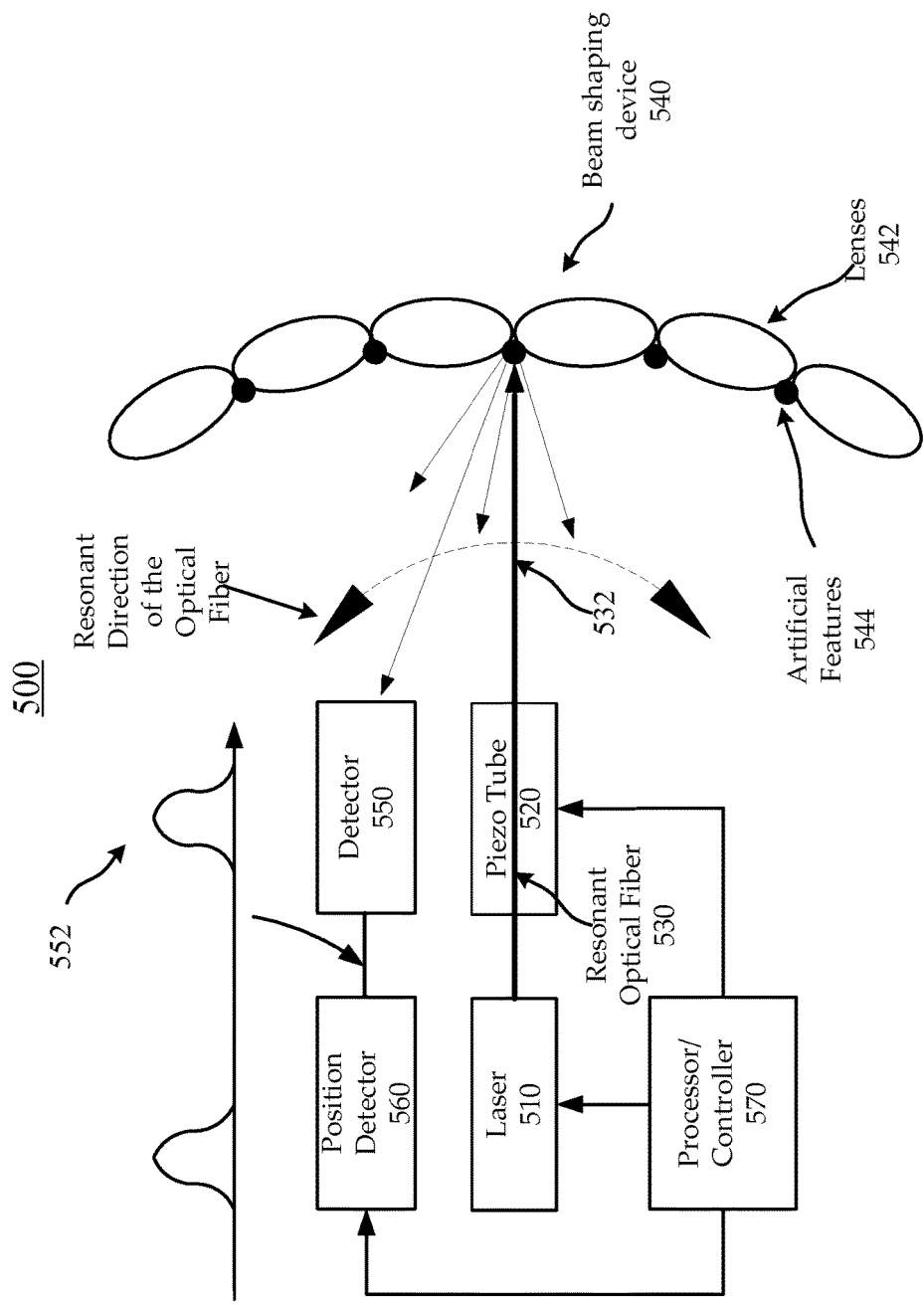
FIG. 5A illustrates an example system using a resonant optical fiber without a beam splitter.

FIG. 5A illustrates an example system 500 using a resonant optical fiber without a beam splitter, according to some embodiments of this disclosure. System 500 may be a LIDAR, LADAR, or other like system. As shown in FIG. 5A, system 500 uses a resonant optical fiber 530 for beam scanning. Optical fiber 530 is coupled to a laser 510 to guide the laser beam from laser 510 to a beam shaping device 540, such as a lens array or a single lens. Resonant optical fiber 530 passes through a piezoelectric tube 520 with a distal end extended beyond piezoelectric tube 520 to form a resonant fiber cantilever 532. Laser 510 may be a pulsed laser such as a mode-locked laser as described above with respect to FIGS. 1 and 2.

As also described above with respect to FIG. 2, piezoelectric tube 520 may stimulate optical fiber 530 in one or two dimensions and control the resonant amplitude and/or frequency of the resonant fiber cantilever 532. The resonance of resonant fiber cantilever 532 may be caused and controlled by other mechanisms, such as other electromechanical devices, electromagnetic devices, or acoustic devices. A scan pattern created by the vibration of resonant fiber cantilever 532 may be a linear pattern, a circular pattern, a spiral pattern, a zig-zag pattern, a 2-D pattern including multiple linear patterns, etc. The optical fiber may be a single-mode optical fiber, a multi-mode optical fiber, or a bundle of optical fibers.

Beam shaping device 540 may include a lens or a lens array. Using a lens array may have several advantages over using a single lens for beam shaping in a system. However, dead zones may exist between lenses 542 in an array, and the beam scanning direction may change abruptly when the scanning beam crosses the lens boundary. Finding accurate beam positions within a lens array may be more difficult and may demand greater precision than finding beam positions within a single lens due to gaps between lenses and a greater angular amplification by a lens array compared with a single lens. It is desirable to know with very good accuracy which side of the boundary of a lens the beam is on.

In some embodiments, an artificial feature 544, such as a reflective coating, may be made in areas adjacent to boundaries of lenses 542 within a lens array, such as in areas between lenses 542 or areas including the boundaries of lenses 542. In some embodiments, the reflective coating may form a Lambertian reflector that causes diffusion or scattering. In some embodiments, the reflective coating may cause flared reflection in predetermined directions. The reflective coating may significantly increase the amount of reflected light when a laser beam irradiates the boundary of two lenses 542 in the lens array. A direct hit on the reflective coating may produce a large reflection. A partial hit with part of the light beam entering a lens and part of the light beam hitting the reflective coating may produce a smaller reflection. Thus, when the light beam crosses the boundary between two lenses in a lens array, the amount of reflected light may increase first and then decrease, forming a pulse. The reflected pulse of light may be collected by a detector to produce a pulse as shown in detected signal 552.

Detector 550 may be a high speed photodetector, such as a PIN photodiode or an APD detector, and may be positioned on the same side of beam shaping device 540 as laser 510 to detect the reflected laser beam. In some embodiments, a single detector may be used for laser beam position determination. In some embodiments, a plurality of detectors may be used to achieve a better accuracy of laser beam position determination. The detected signals 552 from detector 550 may then be sent to position detector 560 for determining the current position of the laser beam on beam shaping device 540. With known approximate speed and direction of the resonance of resonant fiber cantilever, the amplitude and/or profile of the pulses of reflected light detected by detector 550 (even if it is a single detector) may be used to form an image of the lens boundary and determine the exact beam position using, for example, sparse sampling techniques. System 500 may also include a processor/controller 570 that can control the operations of laser 510, piezoelectric tube 520, and position detector 560, or perform the functions of position detector 560, similar to processor/controller 410 described above with respect to FIG. 4.

The position of the laser beam may be determined as follows in system 500. Based on the approximate linear/angular speed and direction of the vibration of the resonant fiber cantilever, the approximate position of the laser beam on beam shaping device 540 (for example, the lens number near the laser beam) at a given time may be determined. Based on the profile of the detected pulse, the time when the laser beam crosses the lens boundary may be determined. The position of the laser beam at the given time can then be determined based on the time the laser beam crosses the lens boundary and the speed of the vibration of the resonant fiber cantilever. Alternatively, the position of the laser beam at the given time may be determined by interpolation using the times the laser beam crosses two lens boundaries.

In some systems, a micro-electro-mechanical (MEMS) device, rather than a resonant optical fiber, may be used to scan a laser beam. Reflected light from artificial features on the beam shaping device can be detected and used to determine the exact beam position based on the approximate speed and direction of the MEMS device as described above.

In various embodiments, the lens array in beam shaping device 540 may be a refractive lens array or a diffractive lens array such as a Fresnel lens array or holographic lens array. The lenses in the lens array may be arranged on a plane or on a curved surface as shown in FIG. 5A. In some systems, the lens array may be a one-dimensional lens array. In some systems, the lens array may be a two-dimensional or three-dimensional array. In some systems, the lens or lens array may be formed using electro-optical (EO) material, such as liquid crystal or EO crystal.

In some embodiments, rather than a reflective coating, artificial features 544 may include diffractive optical elements, for example, a blazed grating, such as an Echelle grating, that has a predetermined blaze angle. The blazed grating may be a reflection grating or a transmission grating. For example, the blazed grating may direct the incoming laser beam back to the side of beam shaping device 540 where laser 510 is located or direct the incoming laser beam to a location on the other side of beam shaping device 540.

In some embodiments, the artificial features may be formed using materials with strong absorption at the wavelength of the laser beam. For example, the artificial features may include a photovoltaic material that can convert the incident light into electrical signals and thus can act as a detector. The detected signals may be sent to position detector 560 or processor/controller 570 using, for example, transparent electrodes such as indium tin oxide (ITO) electrodes. In such systems, detector 550 and/or position detector 560 may be omitted. In some embodiments, the artificial features may include a photo luminescent material that can convert the incoming laser beam into light at a different wavelength and thus would not interfere with the light reflected from the target.

In implementations where beam shaping device 540 is a single lens, features such as thin lines, particles, or dents may be made on a surface of the lens or inside the lens. The locations of the features can be predetermined or measured after fabrication. One or more detectors may be used to detect light reflected by the features made on the lens.

Figure 5C:
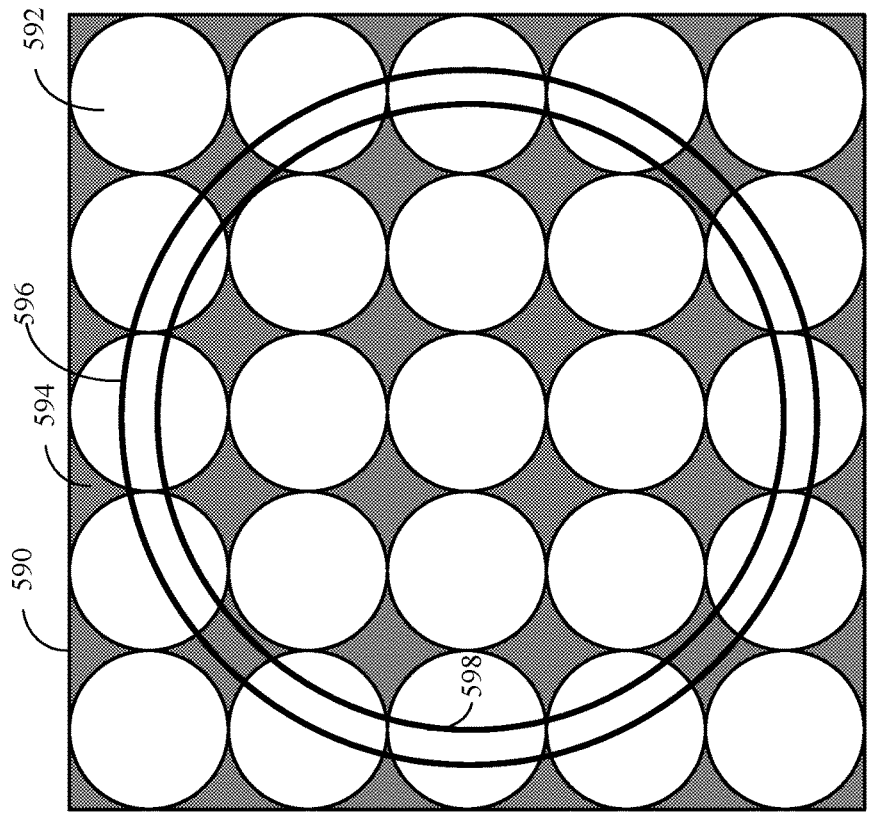
FIG. 5C illustrates an example two-dimensional scan pattern on a beam shaping device using an example system of FIG. 5A.
Figure 5B:
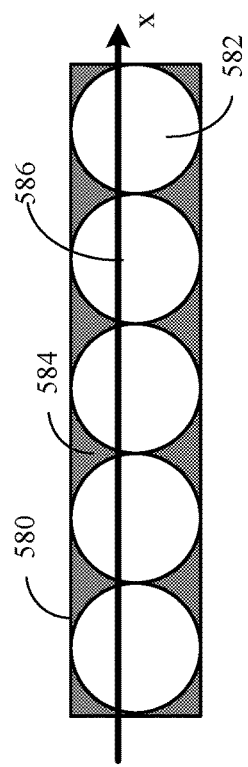
FIG. 5B illustrates an example one-dimensional scan pattern on a beam shaping device using an example system of FIG. 5A.

FIG. 5B illustrates an example one-dimensional scan pattern 586 on a beam shaping device 580 using an example system 500 of FIG. 5A. Beam shaping device 580 may include a plurality of lenses 582 arranged in a 1-D, 2-D, or 3-D array. The gaps 584 between lenses 582 may be coated with reflective material. Thus, when a laser beam scans along scan pattern 586, the amount of reflected laser beam may increase from a low value (when the scanning laser beam is on a lens 582) to a high value (when the scanning laser beam is on a gap 584) and then decrease to a low value (when the scanning laser beam is on another lens 582). Based on the approximate speed and direction of the vibration of the resonant fiber cantilever, the approximate position of the laser beam on beam shaping device 580 (the particular lens(es) near the laser beam) at a given time may be determined. Based on the profile of the detected reflection from beam shaping device 580, the time when the scanning laser beam leaves a lens 582 and the time when the scanning laser beam enters the next lens 582 may be determined. The position of the scanning laser beam on beam shaping device 580 in x direction at the given time may then be determined based on the time the laser beam enters a lens 582 and the speed of the vibration of the resonant fiber cantilever. Alternatively, the position of the scanning laser beam at the given time may be determined by interpolation using the times when the laser beam enters and leaves a lens 582.

FIG. 5C illustrates an example two-dimensional scan pattern 596 (and/or 598) on a beam shaping device 590 using an example system 500 of FIG. 5A. Beam shaping device 590 may include a plurality of lenses 592 arranged in a 2-D or 3-D array. The gaps 594 between lenses 592 may be coated with reflective material. As described above with respect to FIG. 5B, when a laser beam scans along scan pattern 596, the amount of reflected laser beam may change depending on the position of the scanning laser beam. Based on the approximate linear/angular speed and direction of the vibration of the resonant fiber cantilever, the approximate position of the laser beam on beam shaping device 590 (the particular lens(es) near the laser beam) at a given time may be determined. Based on the profile of the detected reflection from beam shaping device 590, the time when the laser beam leaves a particular lens and the time when the laser beam enters the next lens may be determined. In some embodiments, based on the approximate position of the laser beam, the designed scan pattern, and the time period between the time when the laser beam leaves a lens and the time when the laser beam enters the next lens, the position where the laser beam leaves a lens and/or the position where the laser beam enters the next lens may be determined. For example, as shown in FIG. 5C, scan pattern 596 and scan pattern 598 may result in different profiles of detected reflection signals. Based on the differences in the profiles of detected reflection signals, the position where the laser beam leaves a lens and/or the position where the laser beam enters the next lens may be determined. In some embodiments, the reflected laser beam from beam shaping device 590 may be detected by a detector array, for example, a 2-D array, and the position where the laser beam leaves a lens and/or the position where the laser beam enters the next lens may be determined based on the reflection signals detected by the 2-D detector array. The position of the scanning laser beam on beam shaping device 590 at the given time may be determined based on the time the laser beam enters a lens 592 and the linear/angular speed of the vibration of the resonant fiber cantilever. Alternatively, the position of the laser beam at the given time may be determined by interpolation using the times the laser beam enters and leaves a lens 592.

Figure 6C:
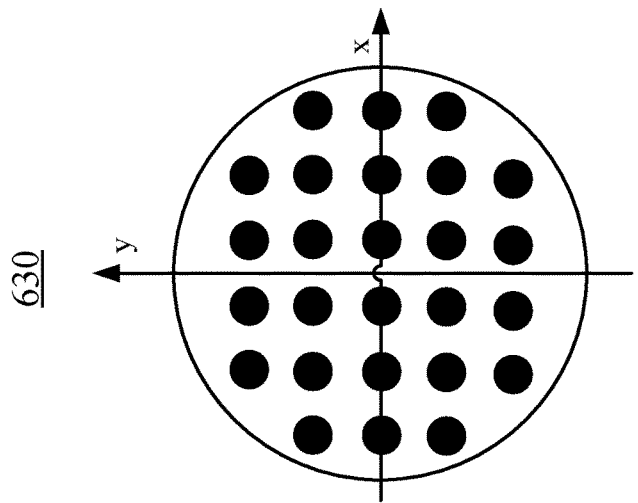
FIG. 6C illustrates individual spots formed on a surface of or inside a lens.
Figure 6B:
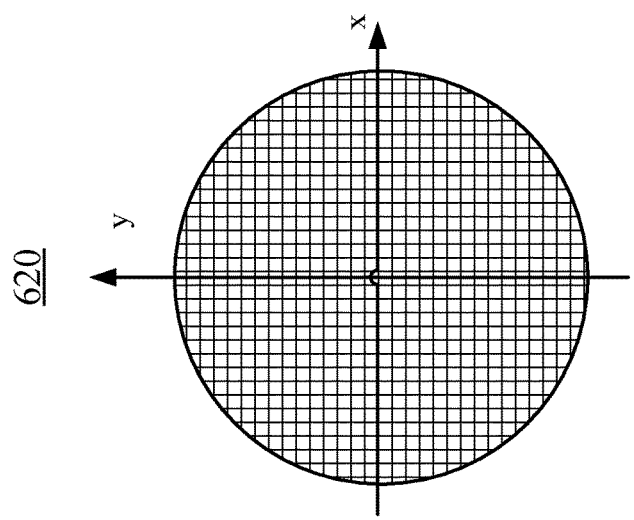
FIG. 6B illustrates thin lines formed on a surface of or inside a lens along two axes to create a matrix.
Figure 6A:
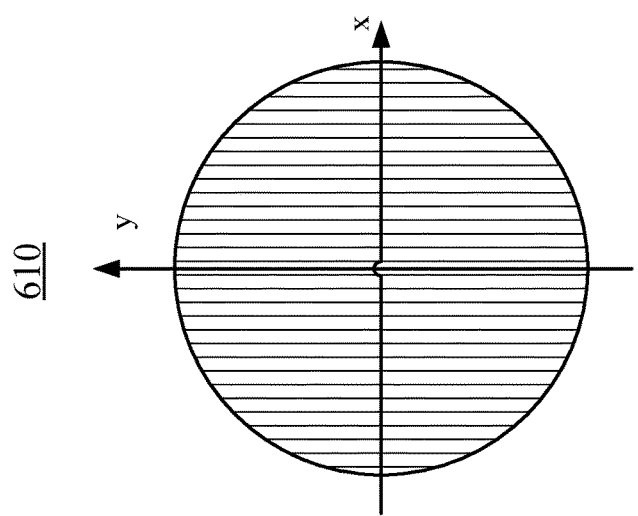
FIG. 6A illustrates thin lines along one axis formed on a surface of or inside a lens.

FIGS. 6A-6C illustrate examples of artificial features on a lens for creating discontinuities in reflection, absorption, or transmission characteristics of the lens, according to some embodiments of the present disclosure. For example, FIG. 6A illustrates thin lines along one axis formed on a surface of or inside a lens 610. The thin lines may be spaced apart evenly or unevenly. In some embodiments, the thin lines may be formed by coating reflective, diffusive, or absorptive material as described above on the surface of the lens. In some embodiments, the thin lines may include grooves formed on the surface of a lens, where the grooves may be filled with reflective, diffusive, or absorptive material as described above.

In examples where a reflective material is coated on the lens, the reflective coating may create discontinuities in the reflective characteristics of the lens. When the light beam is on the reflective coating, a large amount of the light beam is reflected; when the light beam is on other parts of the lens, the amount of light beam reflected is low. Thus, when the light beam crosses a thin line with reflective coating, the amount of reflected light beam increases from a low value to a high value and then decreases to a low value. The profile of the amount of reflected light beam over time is in a shape of a pulse. As a result, the detected signal may include a series of pulses. Based on the approximate speed and direction of the vibration of the resonant fiber cantilever, the approximate position of the laser beam on lens 610 (the particular thin line near the laser beam) at a given time may be determined. Based on the profile of the detected pulse, the time when the laser beam crosses the particular thin line may be determined. The position of the laser beam on the x-axis at the given time can then be determined based on the time the laser beam crosses the particular thin line and the speed of the vibration of the resonant fiber cantilever. Alternatively, the position of the laser beam at the given time may be determined by interpolation using the times the laser beam crosses two thin lines.

In some examples, the thin lines may be formed by coating ITO material and photovoltaic material on the lens, such that incident light may be converted to an electrical signal by the photovoltaic material and conducted by the ITO material. In these examples, based on the position of the thin line that generates the photovoltaic signal and the time when the photovoltaic signal is generated, the position of the laser beam on lens 610 in the x direction at a given time may be determined using the speed of the vibration or by interpolation as described above.

FIG. 6B illustrates thin lines formed on a surface of or inside a lens 620 along two axes to create a matrix. The thin lines in FIG. 6B may be formed as described above with respect to the thin lines in FIG. 6A. The position of the light beam on lens 620 in either x or y direction at a given time can be determined as described above with respect to FIG. 6A.

FIG. 6C illustrates individual spots formed on a surface of or inside a lens 630. For example, the individual spots may be dents formed on the surface of the lens. The dents may be filled with reflective, adsorptive or transmissive material as described above. The individual spots may also be features created inside the lens using reflective, adsorptive or transmissive material as described above. The position of the light beam on lens 630 in either the x or y direction at a given time may be determined as described above with respect to FIG. 6A.

In various systems where the beam shaping device, such as beam shaping device 540 of FIG. 5A, includes a lens array, artificial features may be formed in at least one of areas adjacent to boundaries of lenses as illustrated in FIGS. 5A-5C and described in detail above, or areas on a surface or inside of each lens 542 as illustrated in FIGS. 6A-6C and described in detail above.

Figure 7:
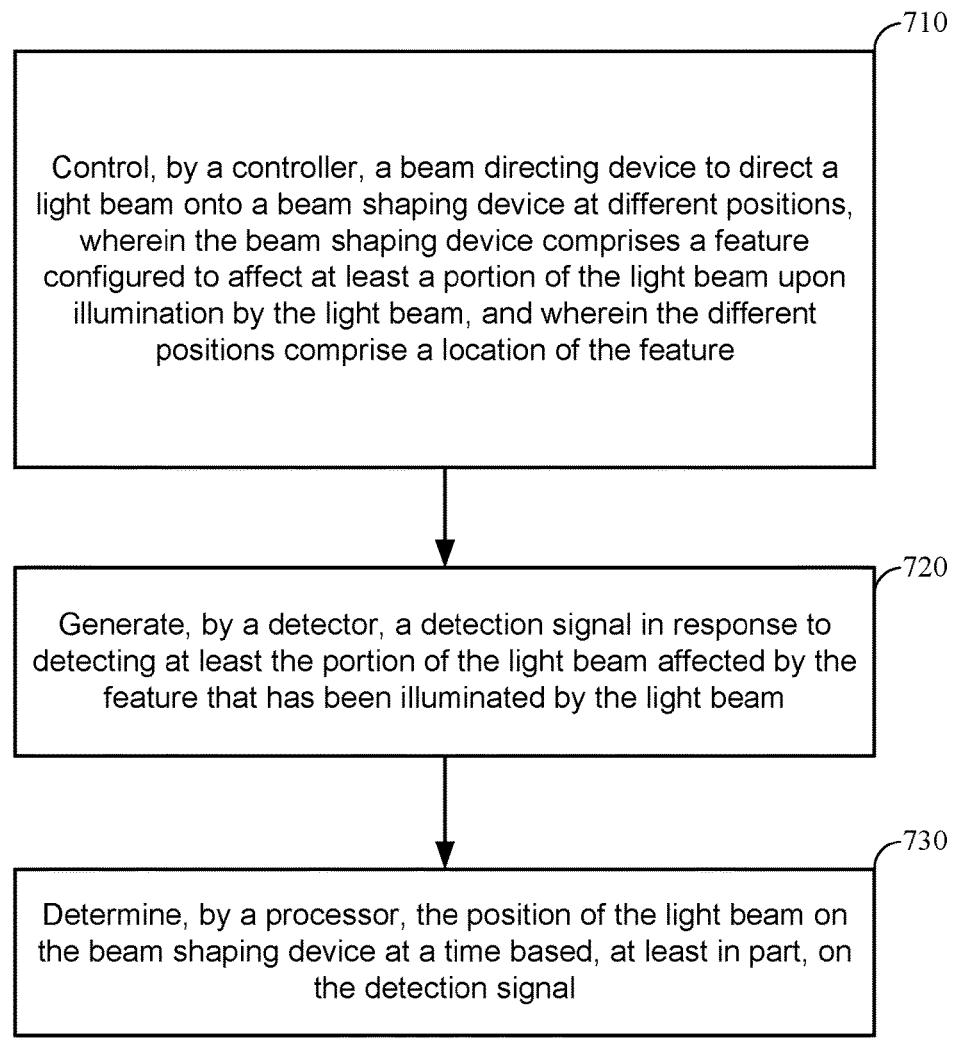
FIG. 7 is a flow chart illustrating an embodiment of a method for detecting light beam position in a system.

FIG. 7 is a flow chart 700 illustrating an embodiment of a method for detecting laser beam position in a system, such as a LIDAR system. It is noted that the disclosed method may be used in systems other than a LIDAR system, for example, inspection systems.

Figure 8:
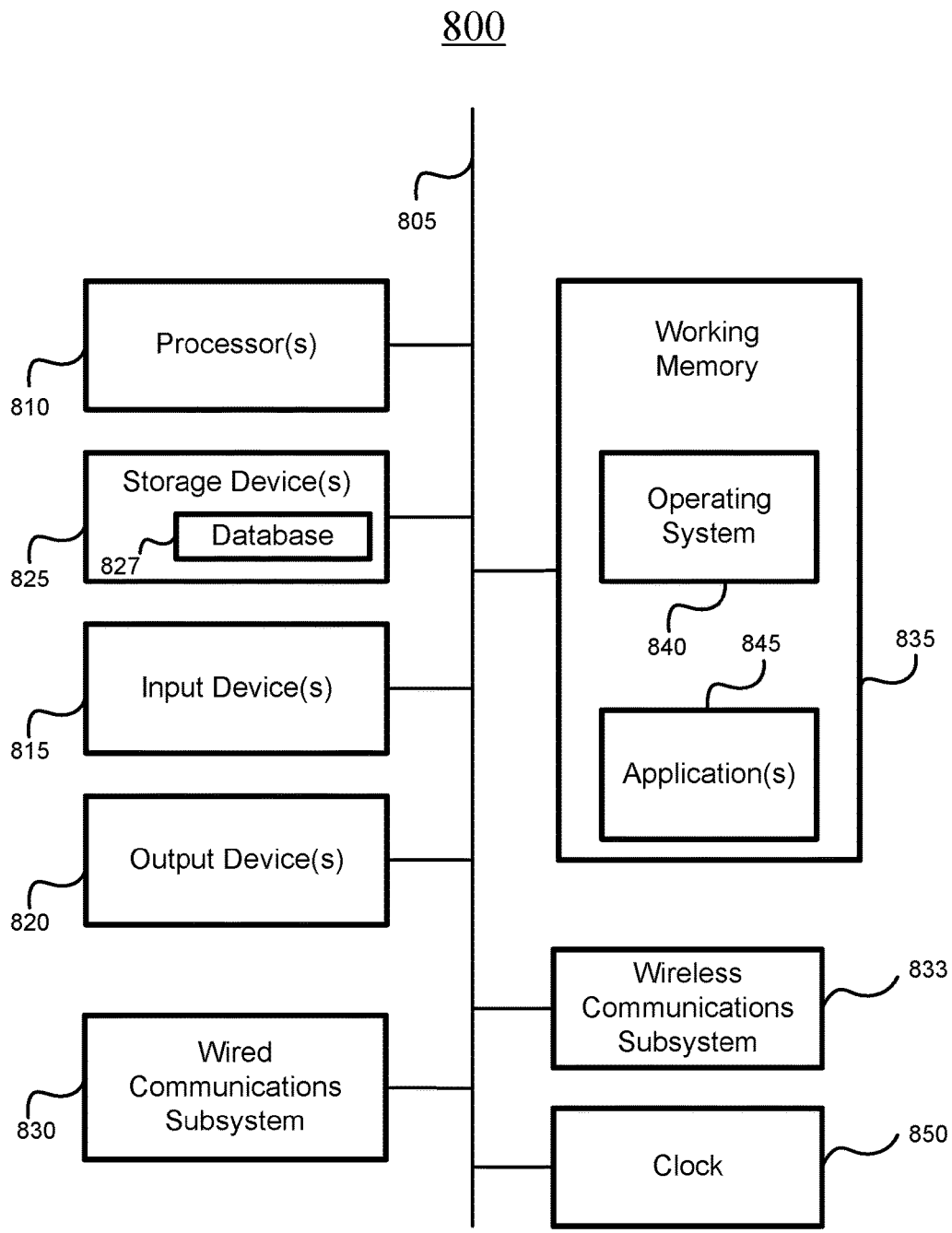
FIG. 8 is a block diagram of an example computing system for implementing some of the examples described herein.

At block 710, a beam directing device, such as resonant optical fibers 230, 432 and 530, actuators 220 and 430, and piezoelectric tube 520, may be controlled by a processor or controller, such as processor/controller 410 and 570, or processor(s) 810 as illustrated in FIG. 8 and described in detail below, to direct a light beam onto a beam shaping device at different positions. The beam shaping device, such as beam shaping device 540 of FIG. 4, lens 610 of FIG. 6A, lens 620 of FIG. 6B, and lens 630 of FIG. 6C, may include a feature formed thereon as described above. The beam shaping device may be configured to collimate, focus, expand, deflect, or otherwise change the wave front of an incoming light beam. The feature may be configured to affect at least a portion of the light beam upon illumination by the light beam by, for example, causing at least one of a detectable change in reflection, a detectable change in transmission, a detectable change in absorption, or a detectable combination thereof, of at least the portion of the light beam, when being illuminated, at least in part, by the light beam. The feature may be configured to cause at least one of an enhanced reflection, an enhanced transmission, an enhanced absorption, or a combination thereof, of the light beam. The different positions may include a location of the feature. As described above, the beam directing device may include different types of actuator, such as a micro-motor, a piezoelectric translator/transducer, a magnetic actuator, or an acoustic actuator. The beam directing device may also include MEMS devices, such as a micro-mirror, rather than a resonant optical fiber. The beam directing device may be configured to scan a light beam in a linear pattern, a circular pattern, a spiral pattern, a zig-zag pattern, or a 2-D pattern including multiple linear patterns. In some embodiments, means for performing the function at block 710 may include, but are not limited to, for example, resonant optical fiber 230 and actuator 220 of FIG. 2, processor/controller 410, resonant optical fiber 432, and actuator 430 of FIG. 4, resonant optical fiber 530, piezoelectric tube 520, and processor/controller 570 of FIG. 5A, and computing system 800 as illustrated in FIG. 8 and described in detail below.

At block 720, a detection signal may be generated by a detector, such as detector 480 or 550, in response to detecting at least the portion of the light beam affected by the feature that has been illuminated by the light beam, such as detecting the detectable change in reflection, the detectable change in transmission, the detectable change in absorption, or the detectable combination thereof, of at least the portion of the light beam. The detection signal may include a series of pulses as illustrated by signal 552 of FIG. 5A. The detection signal from the detector may be received by, for example, processor/controllers 410 and 570 or position detector 560 as described above with respect to FIGS. 4 and 5A, or processor(s) 810 as illustrated in FIG. 8 and described in detail below. In some embodiments, means for performing the function at block 720 may include, but are not limited to, for example, processor/controller 410 and detector 480 of FIG. 4, detector 550, position detector 560, and/or processor/controller 570 of FIG. 5A, and computing system 800 as illustrated in FIG. 8 and described in detail below.

At block 730, based at least partially on the detection signal, a processor, such as processor/controller 410, position detector 560, processor/controller 570, or processor(s) 810 as illustrated in FIG. 8 and described in detail below, may determine the position of the light beam on the beam shaping device at a given time using information such as the approximate linear/angular velocity and the direction of the resonance of the resonant optical fiber. For example, based on the approximate linear/angular velocity and the direction of the resonance of the resonant optical fiber, an approximate position of the light beam at a given time may be determined. Based on the detection signal, a more precise position of the light beam at a given time may be determined using, for example, the time when the light beam crosses the boundary of two lenses and the scanning speed of the light beam. In some embodiments, means for performing the function at block 730 may include, but are not limited to, for example, processor/controller 410 of FIG. 4, position detector 560 and processor/controller 570 of FIG. 5A, and computing system 800 as illustrated in FIG. 8 and described in detail below.

It is noted that even though FIG. 7 describes the operations as a sequential process, some of the operations may be performed in parallel or concurrently. In addition, the order of the operations may be rearranged. An operation may have additional steps not included in the figure. Some operations may be optional, and thus may be omitted in various embodiments. Some operations described in one block may be performed together with operations at another block. Furthermore, embodiments of the methods may be implemented in hardware, software, firmware, middleware, microcode, hardware description languages, or any combination thereof.

FIG. 8 illustrates components of an example computing system 800 for implementing some of the examples described herein. For example, computing system 800 can be used as processor/controller 410 of FIG. 4, position detector 560, or processor/controller 570 of FIG. 5A. It should be noted that FIG. 8 is meant only to provide a generalized illustration of various components, any or all of which may be utilized as appropriate. Moreover, system elements may be implemented in a relatively separated or relatively more integrated manner.

Computing system 800 is shown comprising hardware elements that can be electrically coupled via a bus 805 (or may otherwise be in communication, as appropriate). The hardware elements may include processor(s) 810, one or more input devices 815, and one or more output devices 820. Input device(s) 815 can include without limitation camera(s), a touchscreen, a touch pad, microphone(s), a keyboard, a mouse, button(s), dial(s), switch(es), and/or the like. Output devices 820 may include without limitation a display device, a printer, light emitting diodes (LEDs), speakers, and/or the like.

Processor(s) 810 may include without limitation one or more general-purpose processors, one or more special-purpose processors (such as digital signal processing (DSP) chips, graphics acceleration processors, application specific integrated circuits (ASICs), and/or the like), and/or other processing structures or means, which can be configured to perform one or more of the methods described herein.

Computing system 800 can also include a wired communications subsystem 830 and a wireless communication subsystem 833. Wired communications subsystem 830 and wireless communications subsystem 833 can include, without limitation, a modem, a network interface (wireless, wired, both, or other combination thereof), an infrared communication device, a wireless communication device, and/or a chipset (such as a Bluetooth™ device, an IEEE 802.11 device (e.g., a device utilizing one or more of the IEEE 802.11 standards described herein), a WiFi device, a WiMax device, cellular communication facilities, etc.), and/or the like. Subcomponents of the network interface may vary, depending on the type of computing system 800. Wired communications subsystem 830 and wireless communications subsystem 833 may include one or more input and/or output communication interfaces to permit data to be exchanged with a data network, wireless access points, other computer systems, and/or any other devices described herein.

Depending on desired functionality, wireless communication subsystem 833 may include separate transceivers to communicate with base transceiver stations and other wireless devices and access points, which may include communicating with different data networks and/or network types, such as wireless wide-area networks (WWANs), wireless local area networks (WLANs), or wireless personal area networks (WPANs). A WWAN may be, for example, a WiMax (IEEE 1002.16) network. A WLAN may be, for example, an IEEE 802.11x network. A WPAN may be, for example, a Bluetooth network, an IEEE 802.15x, or some other types of network. The techniques described herein may also be used for any combination of WWAN, WLAN and/or WPAN.

Computer system 800 of FIG. 8 may include a clock 850 on bus 805, which can generate a signal to synchronize the various components on bus 805. Clock 850 may include an LC oscillator, a crystal oscillator, a ring oscillator, a digital clock generator such as a clock divider or clock multiplexer, a phase locked loop, or other clock generator. The clock may be synchronized (or substantially synchronized) with corresponding clocks on other devices while performing the techniques described herein.

Computing system 800 may further include (and/or be in communication with) one or more non-transitory storage devices 825, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable and/or the like. Such storage devices may be configured to implement any appropriate data stores, including without limitation, various file systems, database structures, and/or the like. For instance, storage device(s) 825 may include a database 827 (or other data structure) configured to store detected signals as described in embodiments herein.

In many embodiments, computing system 800 may further comprise a working memory 835, which can include a RAM or ROM device, as described above. Software elements, shown as being currently located within working memory 835, can include an operating system 840, device drivers, executable libraries, and/or other code, such as one or more application programs 845, which may comprise software programs provided by various embodiments, and/or may be designed to implement methods, and/or configure systems, provided by other embodiments, as described herein, such as some or all of the methods described in relation to FIG. 7. Merely by way of example, one or more procedures described with respect to the method discussed above might be implemented as code and/or instructions executable by a computer (and/or a processor within a computer). In an aspect, such code and/or instructions can be used to configure and/or adapt a general purpose computer (or other device) to perform one or more operations in accordance with the described methods.

A set of these instructions and/or code might be stored on a non-transitory computer-readable storage medium, such as non-transitory storage device(s) 825 described above. In some cases, the storage medium might be incorporated within a computer system, such as computing system 800. In other embodiments, the storage medium might be separate from a computer system (e.g., a removable medium, such as a flash drive), and/or provided in an installation package, such that the storage medium can be used to program, configure, and/or adapt a general purpose computer with the instructions/code stored thereon. These instructions might take the form of executable code, which is executable by computing system 800 and/or might take the form of source and/or installable code, which, upon compilation and/or installation on computing system 800 (e.g., using any of a variety of generally available compilers, installation programs, compression/decompression utilities, etc.), then takes the form of executable code.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

With reference to the appended figures, components that can include memory can include non-transitory machine-readable media. The terms "machine-readable medium" and "computer-readable medium" as used herein, refer to any storage medium that participates in providing data that causes a machine to operate in a specific fashion. In embodiments provided hereinabove, various machine-readable media might be involved in providing instructions/code to processors and/or other device(s) for execution. Additionally or alternatively, the machine-readable media might be used to store and/or carry such instructions/code. In many implementations, a computer-readable medium is a physical and/or tangible storage medium. Such a medium may take many forms, including but not limited to, non-volatile media, volatile media, and transmission media. Common forms of computer-readable media include, for example, magnetic and/or optical media, punch cards, paper tape, any other physical medium with patterns of holes, a RAM, a PROM, EPROM, a FLASH-EPROM, any other memory chip or cartridge, a carrier wave as described hereinafter, or any other medium from which a computer can read instructions and/or code.

The methods, systems, and devices discussed herein are examples. Various embodiments may omit, substitute, or add various procedures or components as appropriate. For instance, features described with respect to certain embodiments may be combined in various other embodiments. Different aspects and elements of the embodiments may be combined in a similar manner. The various components of the figures provided herein can be embodied in hardware and/or software. Also, technology evolves and, thus, many of the elements are examples that do not limit the scope of the disclosure to those specific examples.

It has proven convenient at times, principally for reasons of common usage, to refer to such signals as bits, information, values, elements, symbols, characters, variables, terms, numbers, numerals, or the like. It should be understood, however, that all of these or similar terms are to be associated with appropriate physical quantities and are merely convenient labels. Unless specifically stated otherwise, as is apparent from the discussion above, it is appreciated that throughout this specification discussions utilizing terms such as "processing," "computing," "calculating," "determining," "ascertaining," "identifying," "associating," "measuring," "performing," or the like refer to actions or processes of a specific apparatus, such as a special purpose computer or a similar special purpose electronic computing device. In the context of this specification, therefore, a special purpose computer or a similar special purpose electronic computing device is capable of manipulating or transforming signals, typically represented as physical electronic, electrical, or magnetic quantities within memories, registers, or other information storage devices, transmission devices, or display devices of the special purpose computer or similar special purpose electronic computing device.

Those of skill in the art will appreciate that information and signals used to communicate the messages described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Terms, "and," "or," and "an/or," as used herein, may include a variety of meanings that also is expected to depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein may be used to describe any feature, structure, or characteristic in the singular or may be used to describe some combination of features, structures, or characteristics. However, it should be noted that this is merely an illustrative example and claimed subject matter is not limited to this example. Furthermore, the term "at least one of" if used to associate a list, such as A, B, or C, can be interpreted to mean any combination of A, B, and/or C, such as A, AB, AA, AAB, AABBCCC, etc.

Reference throughout this specification to "one example", "an example", "certain examples", or "exemplary implementation" means that a particular feature, structure, or characteristic described in connection with the feature and/or example may be included in at least one feature and/or example of claimed subject matter. Thus, the appearances of the phrase "in one example", "an example", "in certain examples" or "in certain implementations" or other like phrases in various places throughout this specification are not necessarily all referring to the same feature, example, and/or limitation. Furthermore, the particular features, structures, or characteristics may be combined in one or more examples and/or features.

Some portions of the detailed description included herein may be presented in terms of algorithms or symbolic representations of operations on binary digital signals stored within a memory of a specific apparatus or special purpose computing device or platform. In the context of this particular specification, the term specific apparatus or the like includes a general purpose computer once it is programmed to perform particular operations pursuant to instructions from program software. Algorithmic descriptions or symbolic representations are examples of techniques used by those of ordinary skill in the signal processing or related arts to convey the substance of their work to others skilled in the art. An algorithm is here, and generally, is considered to be a self-consistent sequence of operations or similar signal processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals, or the like. It should be understood, however, that all of these or similar terms are to be associated with appropriate physical quantities and are merely convenient labels. Unless specifically stated otherwise, as apparent from the discussion herein, it is appreciated that throughout this specification discussions utilizing terms such as "processing," "computing," "calculating," "determining" or the like refer to actions or processes of a specific apparatus, such as a special purpose computer, special purpose computing apparatus or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of the special purpose computer or similar special purpose electronic computing device.

In the preceding detailed description, numerous specific details have been set forth to provide a thorough understanding of claimed subject matter. However, it will be understood by those skilled in the art that claimed subject matter may be practiced without these specific details. In other instances, methods and apparatuses that would be known by one of ordinary skill have not been described in detail so as not to obscure claimed subject matter. Therefore, it is intended that claimed subject matter not be limited to the particular examples disclosed, but that such claimed subject matter may also include all aspects falling within the scope of appended claims, and equivalents thereof.

For an implementation involving firmware and/or software, the methodologies may be implemented with modules (e.g., procedures, functions, and so on) that perform the functions described herein. Any machine-readable medium tangibly embodying instructions may be used in implementing the methodologies described herein. For example, software codes may be stored in a memory and executed by a processor unit. Memory may be implemented within the processor unit or external to the processor unit. As used herein the term "memory" refers to any type of long term, short term, volatile, nonvolatile, or other memory and is not to be limited to any particular type of memory or number of memories, or type of media upon which memory is stored.

If implemented in firmware and/or software, the functions may be stored as one or more instructions or code on a computer-readable storage medium. Examples include computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise RAM, ROM, EEPROM, CD-ROM or other optical disk storage, magnetic disk storage, semiconductor storage, or other storage devices, or any other medium that can be used to store desired program code in the form of instructions or data structures and that can be accessed by a computer; disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

In addition to storage on computer-readable storage medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims. That is, the communication apparatus includes transmission media with signals indicative of information to perform disclosed functions. At a first time, the transmission media included in the communication apparatus may include a first portion of the information to perform the disclosed functions, while at a second time the transmission media included in the communication apparatus may include a second portion of the information to perform the disclosed functions.

What is claimed is:

1. A system comprising:
a beam shaping device comprising a feature formed on or inside the beam shaping device configured to affect at least a portion of a light beam upon illumination by the light beam, the beam shaping device configured to illuminate a point on a target with the light beam;
a beam directing device configured to direct the light beam onto the beam shaping device at different positions, wherein the different positions comprise a location of the feature formed on or inside the beam shaping device;
an optical detector configured to generate a feature detection signal in response to detecting at least the portion of the light beam affected by the feature formed on or inside the beam shaping device that has been illuminated by the light beam; and
a processor configured to determine a position of the light beam on the beam shaping device at a time based, at least in part, on the feature detection signal.

2. The system of claim 1,
wherein the light beam comprises a laser beam; and
wherein the beam shaping device is configured to illuminate the point on the target with the laser beam.

3. The system of claim 1,
wherein the beam shaping device comprises a lens; and
wherein the feature formed on or inside the beam shaping device comprises at least one of a line, a dent, or a particle formed on a surface of the lens or inside the lens.

4. The system of claim 1,
wherein the beam shaping device comprises a plurality of lenses; and
wherein the feature formed on or inside the beam shaping device comprises a reflective coating in an area at a boundary of two lenses in the plurality of lenses.

5. The system of claim 4, wherein the plurality of lenses is arranged in one of a one-dimensional array, a two-dimensional array, and a three-dimensional array.

6. The system of claim 1, wherein the feature formed on or inside the beam shaping device is configured to affect at least the portion of the light beam upon illumination by the light beam by causing at least one of:
   i) a detectable change in reflection of at least the portion of the light beam,
   ii) a detectable change in transmission of at least the portion of the light beam,
   iii) a detectable change in absorption of at least the portion of the light beam, or
   iv) a detectable combination thereof.

7. The system of claim 1, wherein the beam directing device comprises an optical fiber configured to guide the light beam and vibrate upon stimulation, such that the light beam is directed onto the beam shaping device at different positions when the optical fiber vibrates.

8. The system of claim 7, wherein the optical fiber comprises a cantilever portion having a floating end.

9. The system of claim 7, wherein the beam directing device comprises an actuator configured to stimulate the optical fiber such that the vibration of the optical fiber results in a predetermined scan pattern of the light beam.

10. The system of claim 9, wherein the actuator comprises one of a piezoelectric tube, a micro-electro-mechanical system (MEMS) actuator, an electromagnetic actuator, and an acoustic actuator.

11. The system of claim 1, further comprising:
a pulsed fiber laser configured to generate the light beam.

12. A method for use in detecting a position of a light beam, the method comprising:
controlling, by a controller, a beam directing device to direct the light beam onto a beam shaping device at different positions,
   wherein the beam shaping device comprises a feature formed on or inside the beam shaping device configured to affect at least a portion of the light beam upon illumination by the light beam, the beam shaping device configured to illuminate a point on a target with the light beam; and
   wherein the different positions comprise a location of the feature formed on or inside the beam shaping device;
generating, by a detector, a detection signal in response to detecting at least the portion of the light beam affected by the feature formed on or inside the beam shaping device that has been illuminated by the light beam; and
determining, by a processor, the position of the light beam on the beam shaping device at a time based, at least in part, on the detection signal.

13. The method of claim 12,
wherein the light beam comprises a laser beam; and
wherein the beam shaping device is configured to illuminate the point on the target with the laser beam.

14. The method of claim 12, wherein the feature formed on or inside the beam shaping device is configured to affect at least the portion of the light beam upon illumination by the light beam by causing at least one of:
   i) a detectable change in reflection of at least the portion of the light beam,
   ii) a detectable change in transmission of at least the portion of the light beam,
   iii) a detectable change in absorption of at least the portion of the light beam, or
   iv) a detectable combination thereof.

15. The method of claim 12,
wherein the beam shaping device comprises a lens; and
wherein the feature formed on or inside the beam shaping device comprises at least one of a line, a dent, or a particle formed on a surface of the lens or inside the lens.

16. The method of claim 12,
wherein the beam shaping device comprises a plurality of lenses; and
wherein the feature formed on or inside the beam shaping device comprises a reflective coating in an area at a boundary of two lenses in the plurality of lenses.

17. The method of claim 12, wherein the beam directing device comprises an optical fiber configured to guide the light beam and vibrate upon stimulation, such that the light beam is directed onto the beam shaping device at different positions when the optical fiber vibrates.

18. The method of claim 17, wherein the beam directing device comprises an actuator configured to stimulate the optical fiber such that the vibration of the optical fiber results in a predetermined scan pattern of the light beam.

19. The method of claim 18, wherein the predetermined scan pattern comprises a spiral pattern.

20. The method of claim 18, wherein the actuator comprises one of a piezoelectric tube, a micro-electro-mechanical system (MEMS) actuator, an electromagnetic actuator, and an acoustic actuator.

21. An apparatus comprising:
   means for beam shaping, the means for beam shaping comprising a feature formed on or inside the beam shaping device configured to affect at least a portion of a light beam upon illumination by the light beam, the beam shaping device is configured to illuminate a point on a target with the light beam;
   means for directing the light beam onto the means for beam shaping at different positions, wherein the different positions comprise a location of the feature formed on or inside the beam shaping device;
   means for generating a detection signal in response to detecting at least the portion of the light beam affected by the feature formed on or inside the beam shaping device that has been illuminated by the light beam; and
   means for determining a position of the light beam on the means for beam shaping at a time based, at least in part, on the detection signal.

22. The apparatus of claim 21, wherein the feature formed on or inside the beam shaping device is configured to affect at least the portion of the light beam upon illumination by the light beam by causing at least one of:
   i) a detectable change in reflection of at least the portion of the light beam,
   ii) a detectable change in transmission of at least the portion of the light beam,
   iii) a detectable change in absorption of at least the portion of the light beam, or
   iv) a detectable combination thereof.

23. The apparatus of claim 21,
   wherein the means for beam shaping comprises a lens; and
   wherein the feature formed on or inside the beam shaping device comprises at least one of a line, a dent, or a particle formed on a surface of the lens or inside the lens.

24. The apparatus of claim 21,
   wherein the means for beam shaping comprises a plurality of lenses; and
   wherein the feature formed on or inside the beam shaping device comprises a reflective coating in an area at a boundary of two lenses in the plurality of lenses.

25. A non-transitory computer-readable storage medium including machine-readable instructions stored thereon, the instructions, when executed by one or more processors, causing the one or more processors to:
   control, through a controller, a beam directing device to direct a light beam onto a beam shaping device at different positions,
      wherein the beam shaping device comprises a feature formed on or inside the beam shaping device configured to affect at least a portion of the light beam upon illumination by the light beam, the beam shaping device is configured to illuminate a point on a target with the light beam; and
      wherein the different positions comprise a location of the feature formed on or inside the beam shaping device;
   receive a detection signal generated by a detector in response to detecting at least the portion of the light beam affected by the feature formed on or inside the beam shaping device that has been illuminated by the light beam; and
   determine a position of the light beam on the beam shaping device at a time based, at least in part, on the detection signal.

26. The non-transitory computer-readable storage medium of claim 25, wherein the feature formed on or inside the beam shaping device is configured to affect at least the portion of the light beam upon illumination by the light beam by causing at least one of:
   i) a detectable change in reflection of at least the portion of the light beam,
   ii) a detectable change in transmission of at least the portion of the light beam,
   iii) a detectable change in absorption of at least the portion of the light beam, or
   iv) a detectable combination thereof.

27. The non-transitory computer-readable storage medium of claim 25,
   wherein the beam shaping device comprises a lens; and
   wherein the feature formed on or inside the beam shaping device comprises at least one of a line, a dent, or a particle formed on a surface of the lens or inside the lens.

28. The non-transitory computer-readable storage medium of claim 25,
   wherein the beam shaping device comprises a plurality of lenses; and
   wherein the feature formed on or inside the beam shaping device comprises a reflective coating in an area at a boundary of two lenses in the plurality of lenses.

29. The non-transitory computer-readable storage medium of claim 25, wherein the beam directing device comprises an optical fiber configured to guide the light beam and vibrate upon stimulation, such that the light beam is directed onto the beam shaping device at different positions when the optical fiber vibrates.

30. The non-transitory computer-readable storage medium of claim 29, wherein the beam directing device comprises an actuator configured to stimulate the optical fiber such that the vibration of the optical fiber results in a predetermined scan pattern of the light beam.

* * * * *